(12) United States Patent
Piccin et al.

(10) Patent No.: US 9,782,224 B2
(45) Date of Patent: Oct. 10, 2017

(54) DEVICE FOR GRASPING AN ELONGATED BODY, SUCH AS A NEEDLE, AND ROBOTIZED DEVICE COMPRISING THE SAME

(71) Applicants: UNIVERSITÉ DE STRASBOURG (ÉTABLISSEMENT PUBLIC NATIONAL À CARACTÈRE SCIENTIFIQUE, CULTUREL ET PROFESSIONNEL, Strasbourg (FR); CENTRE NATIONAL DE LA RECHERCHE SCIENTIFIQUE (ÉTABLISSEMENT PUBLIC NATIONAL À CARACTÈRE SCIENTIFIQUE ET TECHNOLOGIQUE, Paris (FR)

(72) Inventors: Olivier Piccin, Mittelhausen (FR); Nitish Kumar, Strasbourg (FR); Laurence Meylheuc, Mittelhausen (FR); Laurent Barbe, Chatenois (FR); Bernard Bayle, Strasbourg (FR); Francois Schmitt, Strasbourg (FR)

(73) Assignees: UNIVERSITE DE STRASBOURG (ETABLISSEMENT PUBLIC NATIONAL A CARACTERE SCIENTIFIQUE, CULTUREL ET PROFESSIONNEL), Strasbourg (FR); CENTRE NATIONAL DE LA RECHERCHE SCIENTIFIQUE (ETABLISSEMENT PUBLIC NATIONAL A CARACTERE SCIENTIFIQUE ET TECHNOLOGIQUE), Paris (FR); INSTITUT HOSPITALO-UNIVERSITAIRE DE CHIRURGIE MINI-INVASIVE (GUIDEE PAR L'IMAGE), Strasbourg (FR); INSTITUT NATIONAL DES SCIENCES APPLIQUEES (ESTABLISSEMENT PUBLIC NATIONAL A CARACTERE SCIENTIFIQUE, CULTUREL ET PROFESSIONNEL), Strasbourg (FR)

( * ) Notice: Subject to any disclaimer, the term of this patent is extended or adjusted under 35 U.S.C. 154(b) by 90 days.

(21) Appl. No.: 14/420,064

(22) PCT Filed: Aug. 9, 2013

(86) PCT No.: PCT/IB2013/002064
§ 371 (c)(1),
(2) Date: Feb. 6, 2015

(87) PCT Pub. No.: WO2014/024038
PCT Pub. Date: Feb. 13, 2014

(65) Prior Publication Data
US 2015/0216604 A1 Aug. 6, 2015

Related U.S. Application Data

(60) Provisional application No. 61/681,264, filed on Aug. 9, 2012.

(51) Int. Cl.
*A61B 17/34* (2006.01)
*A61B 19/00* (2006.01)
(Continued)

(52) U.S. Cl.
CPC ...... *A61B 19/2203* (2013.01); *A61B 17/3403* (2013.01); *A61B 34/30* (2016.02);
(Continued)

(58) Field of Classification Search
CPC ..... A61B 17/3403; A61B 34/30; A61B 34/70; A61B 90/11; A61B 2017/3407;
(Continued)

(56) References Cited

U.S. PATENT DOCUMENTS 2,890,888 A * 6/1959 Dam Ijonaitis ..... B23B 31/1261
279/106
2,980,434 A * 4/1961 Hoffman ............. B23B 31/1269
279/106
(Continued)

FOREIGN PATENT DOCUMENTS

EP 0 187 126 A2 7/1986
WO 2006/035143 A1 4/2006
(Continued)

OTHER PUBLICATIONS

International Search Report, dated Jan. 2, 2014, from corresponding PCT application.

*Primary Examiner* — Tammie K Heller
(74) *Attorney, Agent, or Firm* — Young & Thompson

(57) ABSTRACT

A device for selectively grasping a part of a separate elongated body extending through the device, includes at
(Continued)

least three partially mobile jaw members defining between them a through hole of variable diameter depending on their mutual relative positioning, supporting and driving elements to which the jaw members are mounted and which are adapted to provide a coordinated motion to the members around the elongated body situated in the variable through hole, resulting in a closing or opening of the through hole. The jaw members have an elongated shape with two opposed ends and the supporting and driving elements include a circular or annular support body to which a first end of each jaw member is connected and a mobile annular driving body to which a second opposed end of each jaw member is connected.

19 Claims, 10 Drawing Sheets

(51) Int. Cl.

| | | |
|---|---|---|
| *B23B 31/12* | (2006.01) | |
| *B25J 15/08* | (2006.01) | |
| *B25J 15/10* | (2006.01) | |
| *B25J 15/12* | (2006.01) | |
| *A61B 34/30* | (2016.01) | |
| *A61B 90/11* | (2016.01) | |
| *A61B 17/00* | (2006.01) | |
| *A61B 34/00* | (2016.01) | |

(52) U.S. Cl.
CPC .......... *A61B 90/11* (2016.02); *B23B 31/1261* (2013.01); *B25J 15/086* (2013.01); *B25J 15/10* (2013.01); *B25J 15/12* (2013.01); *A61B 2017/00862* (2013.01); *A61B 2017/00955* (2013.01); *A61B 2017/347* (2013.01); *A61B 2017/3407* (2013.01); *A61B 2017/3409* (2013.01); *A61B 2034/305* (2016.02); *A61B 2034/715* (2016.02)

(58) Field of Classification Search
CPC ...... A61B 2017/347; A61B 2017/3409; B23B 31/1261; B23B 31/1269; B25J 15/083; B25J 15/086; B25J 15/10; B25J 15/12; Y10T 279/17231
See application file for complete search history.

(56) References Cited

U.S. PATENT DOCUMENTS

| | | |
|---|---|---|
| 4,765,669 A | 8/1988 | Meier |
| 2003/0024357 A1 | 2/2003 | Hofmann et al. |
| 2008/0167663 A1 | 7/2008 | De Mathelin et al. |
| 2009/0014907 A1 | 1/2009 | Kuo |

FOREIGN PATENT DOCUMENTS

| | | |
|---|---|---|
| WO | 2006/092496 A1 | 9/2006 |
| WO | 2011/152520 A1 | 12/2011 |

\* cited by examiner

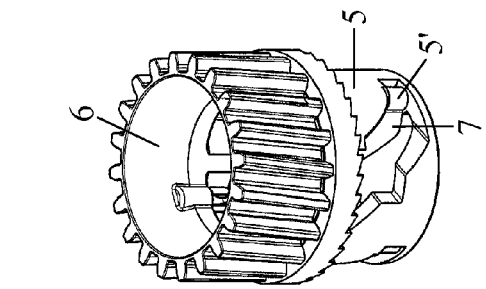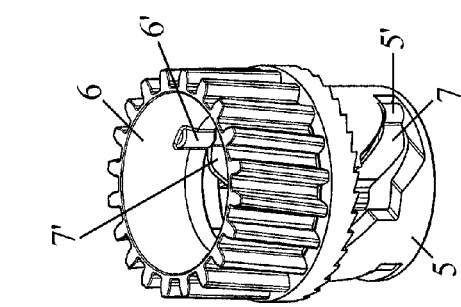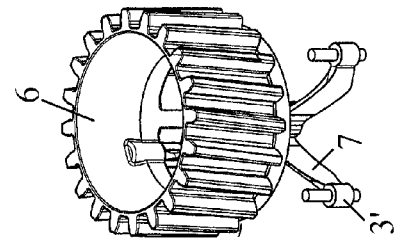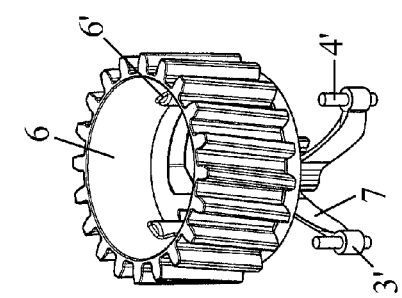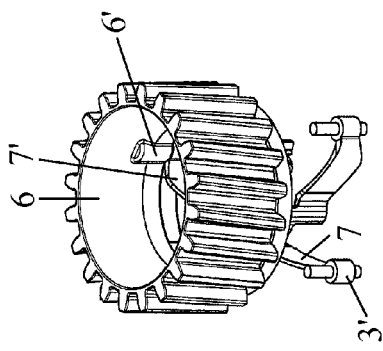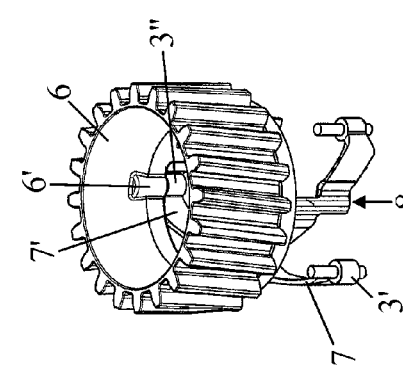

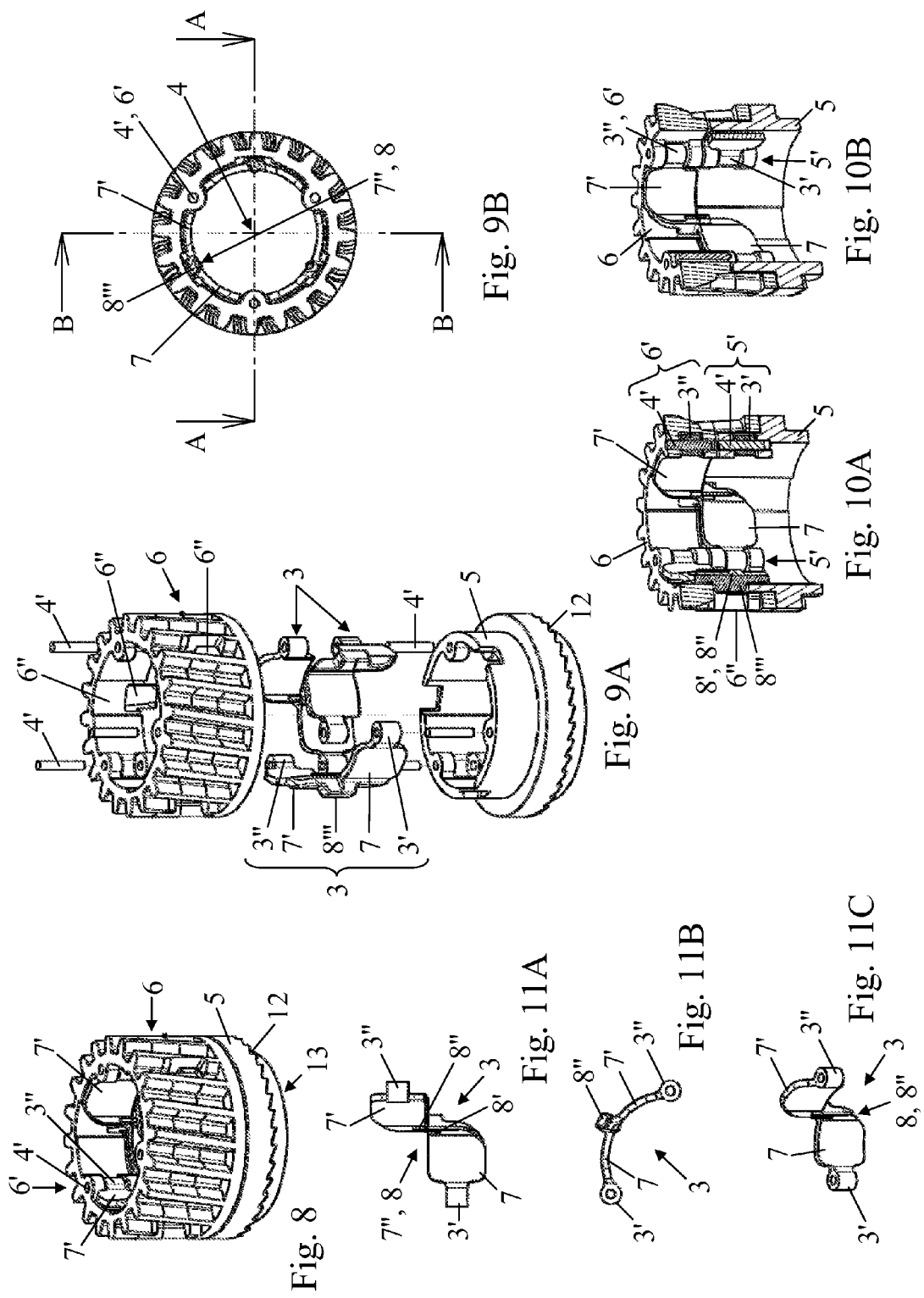

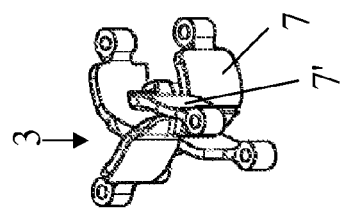
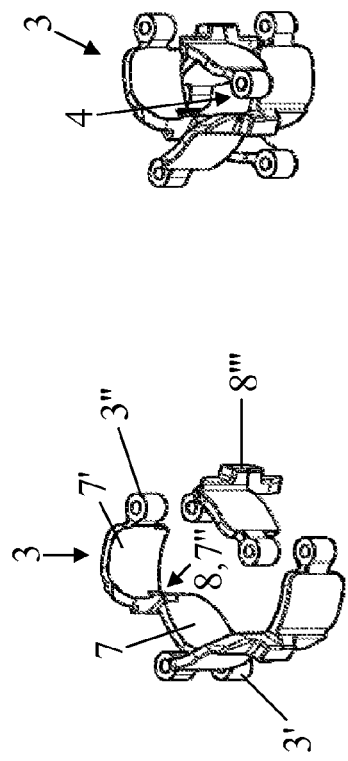
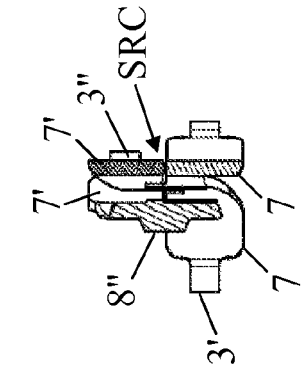
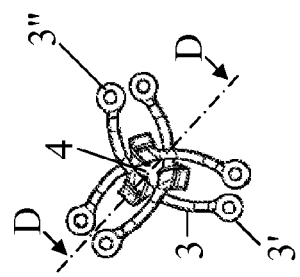
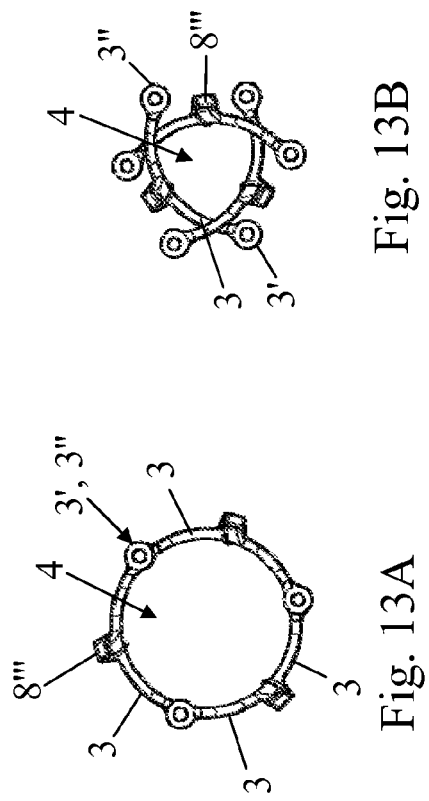

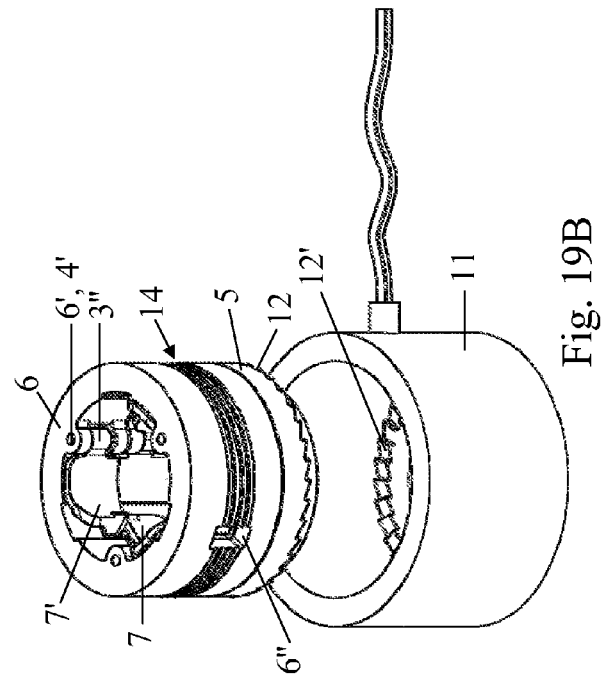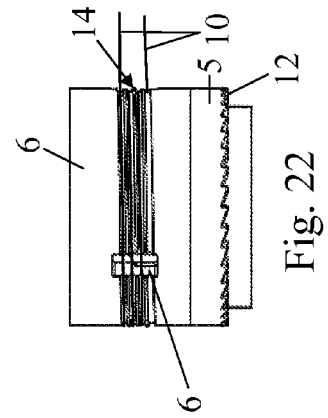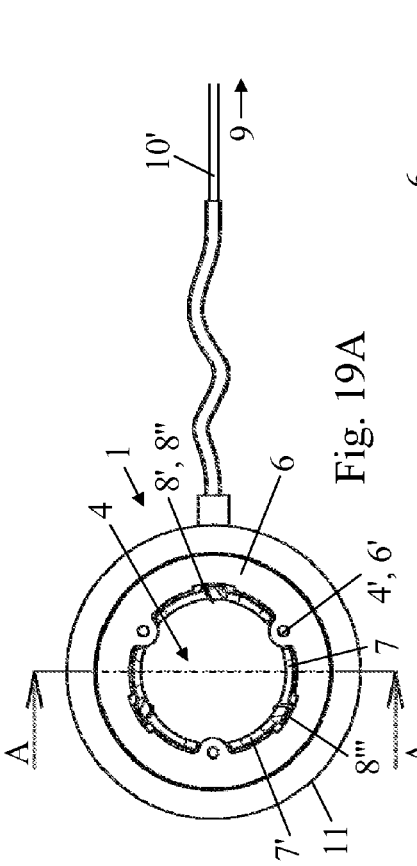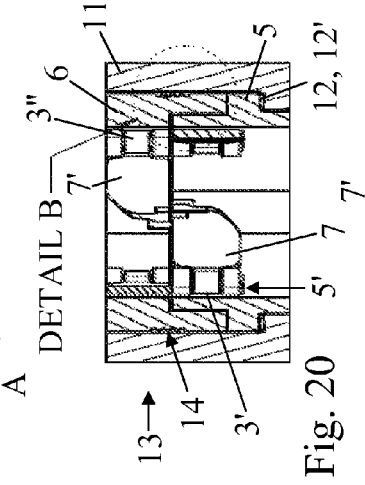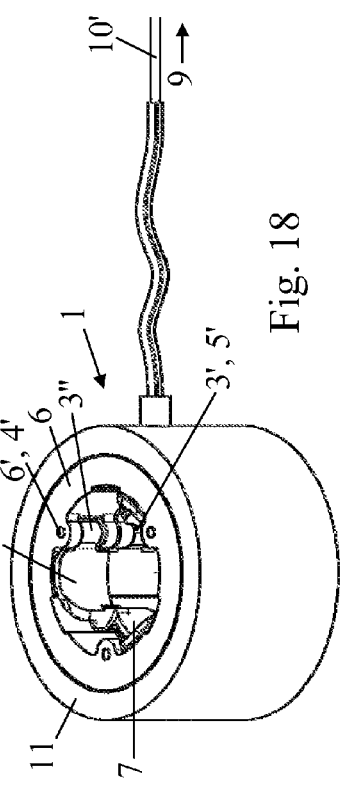

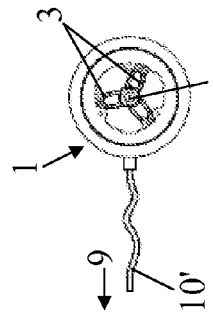
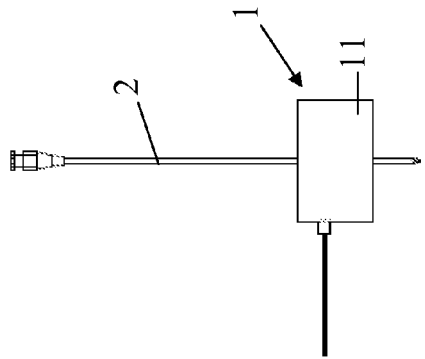
Fig. 24A
Fig. 24B
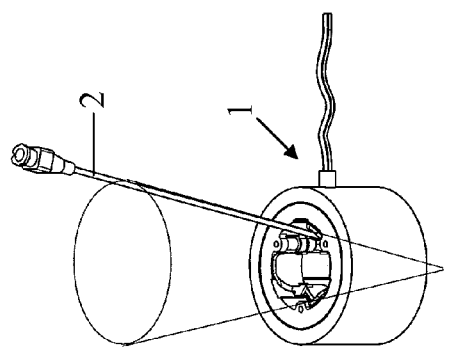
Fig. 23B
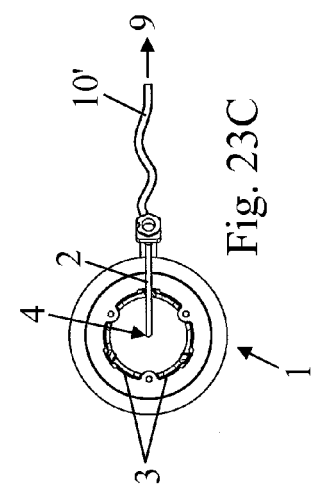
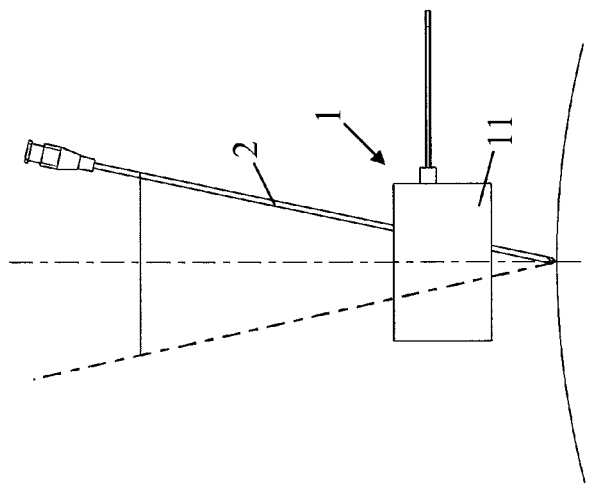
Fig. 23A
Fig. 23C

DEVICE FOR GRASPING AN ELONGATED BODY, SUCH AS A NEEDLE, AND ROBOTIZED DEVICE COMPRISING THE SAME

BACKGROUND OF THE INVENTION

Field of the Invention

The present invention concerns an actuated device for grasping in a controlled manner an elongated body, as well as a robotized device comprising at least one such grasping device and using it to handle said elongated body.

A preferred application context of the invention is the grasping and manipulation of surgical needles which represent a very common concern in many medical specialties involving image guided needle insertions, in particular in the context of interventional radiology.

In this medical specialty, minimally invasive procedures are performed to diagnose or treat pathologies under image guidance.

The medical interventions mainly targeted here encompass the wide class of procedures that necessitate needle insertion such as biopsies, radiofrequency ablations or cancer local delivery treatments.

To ensure a proper safety level in the procedures, visual feedback is usually mandatory to monitor the instrument insertion.

Among the various imaging modalities available, computed tomography (CT) and fluoroscopy provide a fast and accurate visual feedback to the radiologist and are now very widely used in medical routine.

However, repeated CT and fluoroscopy endanger physicians with potentially harmful ionizing radiations.

That is one of the main motivation for developing teleoperated robotic assistant devices to remotely insert needles or similar elongated bodies under CT guidance.

Description of the Related Art

A possible layout of teleoperated percutaneous procedures was presented in Piccin, O., Barbé L., Bayle, B., de Mathelin, M. and Gangi, A., 2009: "Force feedback teleoperated needle insertion device for percutaneous procedures", International Journal of Robotics Research, 28(9), September, pp. 1154-1168, Special issue on Medical Robotics.

It is composed of a master station protected from the radiation source and operated by the physician using a haptic interface.

At the remote site, the slave station comprises the CT scanner, the patient and the robotic assistant dedicated to the percutaneous procedure.

This layout enables the radioprotection of the medical staff but also provides the practitioner with a haptic feedback on the insertion task which is highly desirable for safety reasons.

As a consequence, the development of needle grasping devices is an important subject for the previously targeted applications.

The available space between a CT-scan ring and a patient is a prominent limiting factor. The corresponding volume corresponds typically to a 200 mm radius hemisphere which is just slightly higher than the length of most biopsy needles. Consequently, the grasping device size should be as small as possible.

In addition, it would be beneficial to comply with existing surgical needles, in terms of diameter, length and general constitution, and thus avoid the use of device specific needles.

Another important feature for the needle grasping device is the capacity to allow a wide aperture around the needle when opened as well as to get the needle automatically and necessarily centered during re-grasping of the needle (keeping a secure loose hold on the needle).

This demand originates from the fact that the needle insertion is not a one step task.

Indeed to avoid internal tissue laceration and improve gesture accuracy, the insertion motion itself is generally done during a short patient's apnea. After that, the non-inserted part of the needle requires to be released to comply with the motion exerted by the internal perforated organs.

At this stage, the needle should move freely off a central position about the entry point on the patient's skin.

To perform the following insertion step the grasping device should be capable to re-center and re-grasp the needle.

One optional but very desirable feature of the grasping device corresponds to the possibility of rotating the needle about its axis to facilitate the needle steering.

Concerning force transmission, the grasping device should be able to sustain a maximum insertion action of about 15N, allow haptic feedback, more precisely, and be compatible with real-time insertion force measurement.

To avoid needle deterioration, the grasping device should ideally incorporate a grip limiting scheme.

Concerning the constitutive material requirements, the grasping device should not generate artefacts in CT scanner images.

And the concluding items in this requirement list are the safety and sterilization properties pertaining to the medical context.

Systems dedicated to needle manipulation are very scarce in prior art and literature and use mostly opposing rollers to perform simultaneously the needle grasping as well as its insertion motion (see for examples: Stoianovici, D., Cleary, K., Patriciu, A., Mazilu, D., Stanimir, A., Craciunoiu, N., Watson, V. and Kavoussi, L., 2003: "Acubot: a robot for radiological interventions", Robotics and Automation, IEEE Transactions on, 19(5), October, pp 927-930/Walsch, C. J., Hanumara, N. C., Slocum, A. H., Shepard, J.-A. and Gupta, R., 2008: "A patient-mounted, telerobotic tool for CT-guided percutaneous interventions", Journal of Medical Devices, 2(1), p. 011007.

This working principle makes it very difficult to measure axial insertion forces.

To add this important functionality, it seems necessary to uncouple the needle displacement from its grasping.

This issue has been addressed in the system described in Badaan, S., Petrisor, D., Kim, C., Mozer. P., Mazilu, D., Gruionu, L., Patriciu, A., Cleary, K. and Stoianovici, D., 2011: "Does needle rotation improve lesion targeting?", The International Journal of Medical Robotics and Computer Assisted Surgery", 7(2), pp. 138-147.

But the proposed embodiment does not provide a controlled feature for recentering and gripping back the needle during insertion.

This functionality was included in the needle grasping device disclosed in the previously mentioned publication of Piccin, O. et al.

An other existing solution which allows to overcome the drawbacks of previous devices and achieves to fulfil at least the main requirements exposed herein before, and can be considered as an improvement of the solution of the previously mentioned publication of the International Journal of Robotics Research has been disclosed in EP-A-1 871 26 (US 2008/167663) and in: Piccin, O., Renaud, P., Barbé, L., Bayle, H., Maurin, B. and de Mathelin, M., 2005: "A robotized needle insertion device for percutaneous procedures", In. Proceedings of the 2005 ASME Design Engineering Technical Conferences, pp. 433-440, as several construction embodiments.

In this latter solution, the grasping device consists in at least one annular chuck or mandrel through which the elongated body extends.

Each chuck comprises a main body with a fixed part and a moving part and three jaws which move radially when the moving part is actuated. More precisely, the moving part is in the form of a gear and the jaws are driven by said gear by means of a groove/rib or a rod/slot mechanism, and guided in translation radially.

The chuck can be tightened and opened by rotating the gear member in opposite directions, which causes the jaws to move simultaneously between and extended position near the center of the through passage and a retracted position away from said center, wherein said jaws are located within the thickness of the cylindrical wall of the tubular main body.

Nevertheless, this last existing solution also shows some drawbacks:

1. The grasping force available at the jaws is quite limited, as well as the axial forces applicable to the elongated body;

2. The design and manufacturing of all components, as well as the assembling, need to be done with uttermost precision to achieve simultaneity of movement and centered grasping;

3. The construction design requests that all parts need to be made of rigid material, in particular the components involved in the transmission and transformation of the movement, which latter in addition need to be as small as possible (considering the opposed constraints of limited available free volume and maximum diameter of the through passage in open state), resulting in critical issues as far as manufacturing precision and mechanical slack are concerned (in particular in relation to previous points 1 and 2);

4. A possible jamming of the mechanism cannot be completely avoided (precise translational guiding).

BRIEF SUMMARY OF THE INVENTION

It is a purpose of the present invention to overcome at least some, preferably all, of the main drawbacks indicated previously and to propose an improvement grasping device, making use of the basic principles (chuck unit with jaws) exposed in EP-A-1 871 265.

Therefore, the present invention concerns a device for selectively gripping or grasping a segment or part of a separate elongated body extending through said device, this device comprising at least three, at least partially mobile jaw members or clamping members defining between them a through hole or similar receiving passage of variable diameter depending on their mutual relative positioning, said device comprising also supporting and driving means to which said jaw or clamping members are mounted and/or connected and which are adapted to provide a coordinated motion to said members around the elongated body situated in the variable through hole, resulting in a closing or opening of said through hole, device characterized in that the jaw or clamping members have an elongated shape with to opposed ends and the supporting and driving means mainly comprise a circular or annular support body to which a first end of each jaw or clamping member is connected and a mobile circular or annular driving body to which a second opposed end of each jaw or clamping member is connected, a rotational movement of the driving body relative to the support body resulting in a simultaneous displacement of all the connected second ends of the jaw or clamping members.

BRIEF DESCRIPTION OF THE DRAWINGS

The present invention will be better understood thanks to the following description and drawings of two embodiments of said invention given as non limitative examples thereof, wherein:

FIGS. 4A to 4D are perspective views of the jaws, the mobile or driving body and the fixed or support body of the chuck component of the grasping device in various states of closure of the grasping device;

FIGS. 5A to 5D are perspective views respectively similar to the views of FIGS. 4A to 4D, the support body having been removed;

FIGS. 8, 9A and 9B are respectively perspective, exploded and top views of a [jaw/driving body/support body] assembly or chuck unit which is part of the device illustrated in FIGS. 1A to 1C, showing an alternative design of the jaws and their linkage with the support and driving bodies;

FIGS. 10A and 10B are sectional views along lines A-A and B-B of the item illustrated on FIG. 9B;

FIGS. 11A, 11B and 11C are elevational and perspective views of one of the jaws shown on FIG. 9A;

FIGS. 12A, 12B and 12C are perspective views of the three jaws of the assembly (chuck unit) illustrated in FIGS. 8 and 9, respectively in open state, half closed state and closed state of the grasping device;

FIGS. 13A, 13B and 13C are top views of the jaw arrangements of FIGS. 12A, 12B and 12C respectively;

FIG. 14 is a sectional view along line D-D of the item shown on FIG. 13C, showing the sliding and resting cooperation between upper and lower arms of two jaw members (detail SRC);

FIG. 18 is a perspective view of a second embodiment of an actuated grasping device according to the invention;

FIGS. 19A and 19B are respectively a top view and an exploded view of the device shown on FIG. 8;

FIG. 20 is a sectional view of the device represented on FIG. 19A, along line A-A;

FIG. 21 is a detailed view at a different scale of the detail B of FIG. 10;

FIG. 22 is a side view of the [jaws/driving body/support body] assembly or chuck unit of the device shown in FIGS. 18 and 19, showing the winding of the actuating cable(s) around the driving body;

FIGS. 23A, 23B and 23C are respectively elevational, perspective and top views of the grasping device of FIGS. 18 and 19 with a needle, showing the magnitude of free movement of the needle when the grasping device is in a completely open state, and, FIGS. 24A and 24B are respectively side a top views of the grasping device of FIGS. 18 and 19 firmly holding a needle in a tightened state.

DETAILED DESCRIPTION OF THE PREFERRED EMBODIMENTS

Figure 1A:
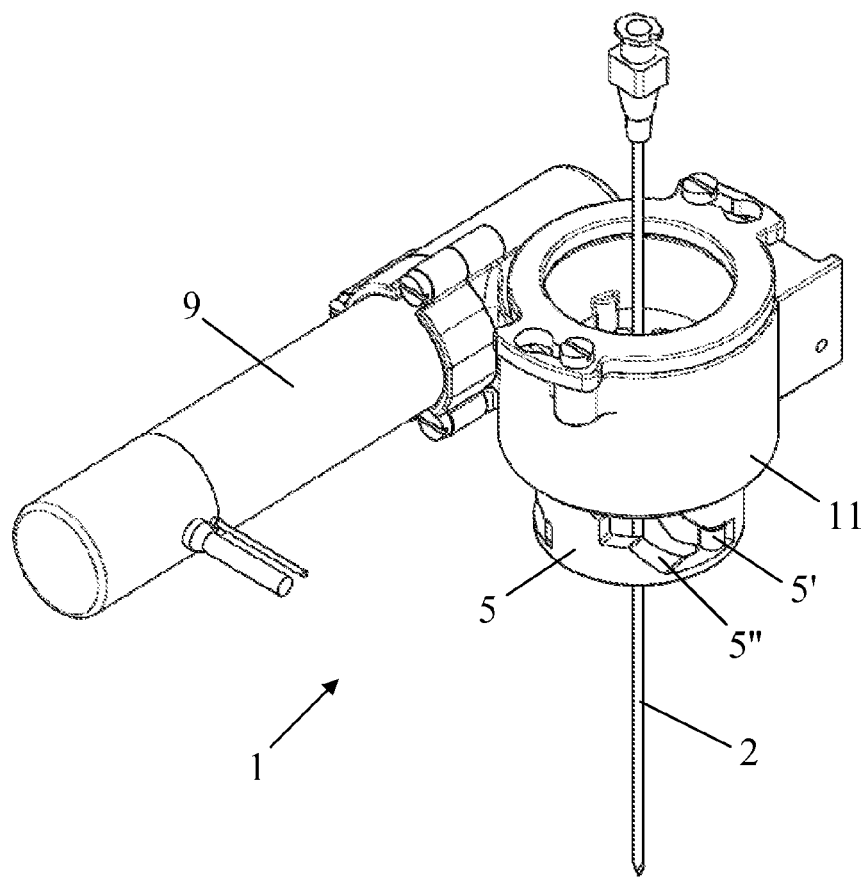
FIGS. 1A and 1B are two perspective views of a first embodiment of an actuated device according to the invention, its jaws being tightened around an elongated cylindrical body in the form of a needle.
Figure 1B:
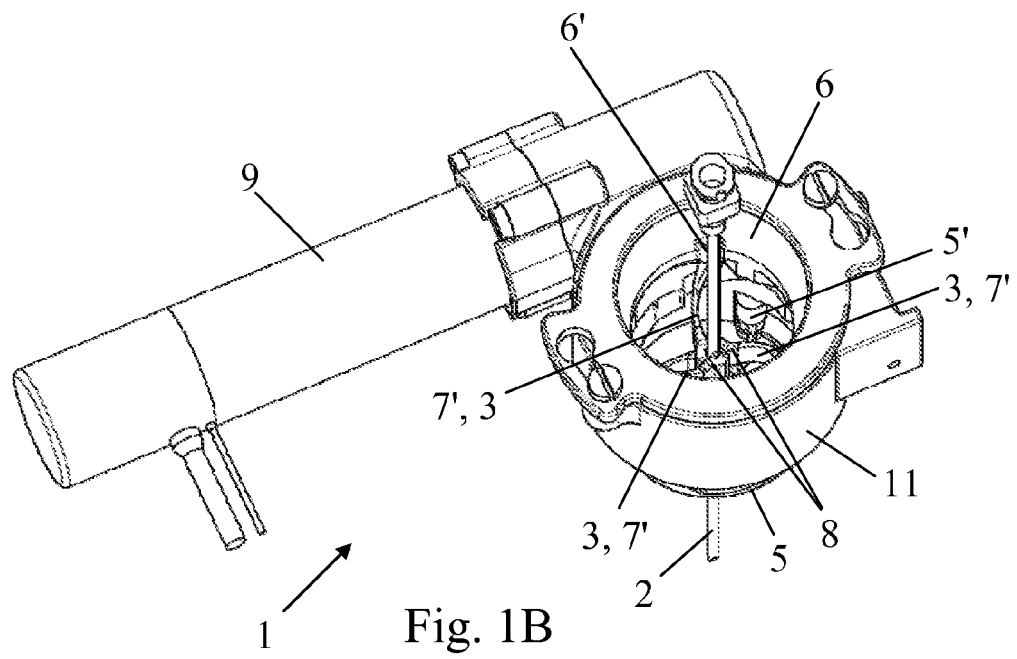

FIGS. 1, 18, 19, 23 and 24 illustrate a device 1 for selectively gripping or grasping a segment or part of a separate elongated body 2 extending through said device. This device 1 comprises at least three, at least partially mobile jaw members or clamping members 3 defining together and between them a through hole or similar receiving passage 4 of variable diameter depending on their mutual relative positioning. This device 1 comprises also supporting and driving means 5, 6 to which said jaw or clamping members 3 are mounted and/or connected and which are adapted to provide a coordinated motion to said members 3 around the elongated body 2 situated in the variable through hole 4, resulting in a closing or opening of said through hole 4.

According to the invention, the jaw or clamping members 3 have an elongated shape with two opposed ends 3', 3" and the supporting and driving means 5, 6 mainly comprise a circular or annular support body 5 to which a first end 3' of each jaw or clamping member 3 is connected and a mobile circular or annular driving body 6 to which a second opposed end 3" of each jaw or clamping member 3 is connected, a rotational movement of the driving body 6 relative to the support body 5 resulting in a simultaneous and synchronous displacement of all the connected second ends 3" of the jaws or clamping members 3 and a corresponding variation of the size of the through hole or passage.

Thus, the jaw members 3 combined with the support and driving bodies 5 and 6 and driven by an actuator 9 (through worm gear 10 or cables 10') form a chuck unit 13 motorized by said actuator 9 and mounted in the casing 11.

In comparison to the previous existing chuck like grasping device, the jaws 3 of the device 1 according to the invention are not submitted to any translatory movement, with the associated limitations, and the direct kinematic link between the jaws 3 and the mobile body 6 ensures the simultaneity of their movement.

As can be best seen on FIGS. 3, 7, 12 and 13, the through hole 4 is not defined by discontinuous and spaced apart jaws as in the previous chuck unit, but by elongated members 3 always extending continually around the through hole 4 whatever the state of opening or closure of the device 1.

These figures also show that the variable through hole 4 itself is actually defined by the mutual intersection of all the sectional areas located on the active clamping side of the at least three jaw members 3.

In accordance with a feature of the invention, illustrated in FIGS. 4 to 7 and 9 to 16, each jaw or clamping member 3 is hinged at its first end 3' with the support body 5 and at its second end 3" with the mobile driving body 6, a relative rotational movement of said mobile body 6 with respect to the fixed support body 5 inducing a rotational displacement of the first end 3' around the axis of its hinged link 5' with the support body 5 and a circular displacement of the second end 3" along a path in the form of a circular arc supported by the inner circumference of the mobile body 6.

This circular displacement of the second end 3" of each member 3 is normally combined with a limited rotational movement of said second end 3" around the axis of its hinged link 6' with said mobile or driving body 6.

Preferably, as shown in FIGS. 2, 7, 11 and 12, each jaw or clamping member 3 consists of an elongated member comprising two brackets or arm portions 7, 7' both connected to a central gripping portion 8 and provided at their opposed first and second ends 3', 3" with male or female components or sites of hinged or pivotal links 5', 6', the complementary female or male components or sites of said links 5', 6' being provided respectively on the support body 5 and on the driving body 6.

The complementary components or sites forming the hinged links 5', 6' may be both female and mutually articulated through a separate pin 4'. Alternatively, one complementary component may be male and the other one female, the pin 4' being formed with the male part.

Advantageously, each jaw or clamping member 3 consists of a partly compliant or flexible elongated member, preferably comprising two surface brackets or arm portions 7, 7' arranged in an offset manner one towards the other, joined together at their abutting ends and hinged respectively with the support and mobile bodies 5 and 6 at the other ends 3', 3", at least a part, in the region 7" of their abutting end, or approximately the major or whole inner surface of said portions 7, 7' forming the gripping portion 8. Thus, bodies of various diameters can be grasped.

To ensure a firmer and progressive grip, the gripping portion 8 may be provided with one or several high frictional soft and/or flexible material projections or pads 8', 8", aligned or not. Preferably, the gripping portion 8 is at least located in the area 7" where the portions or arms 7 and 7' are joined together.

As the jaw members 3 are to define the variable through hole 4 (gripping orifice) also when the device 1 is in a completely open state, the hinged link 5' of one member 3 is preferably axially aligned with the hinged link 6' of the next member 3, when the device is in a completely open state.

To ensure i) an easy functioning of the device 1, without needing a too precise manufacturing, ii) an adaptable and progressively firmer clamping and simultaneously iii) a tolerance free and efficient axial force transmission ability, the jaw or clamping members 3 are advantageously at least partly compliant in a radial direction and substantially rigid in the axial direction, when considered in relation to an elongated body 2, located and grasped within said device 1.

According to a preferred embodiment of the invention, each elongated clamping member 3 has a staggered structure (step-shaped arrangement), the two constitutive brackets or arm portions 7, 7' being shifted one towards the other in the axial direction of the elongated body 2 when said latter is gripped by said cooperating clamping members 3 (FIGS. 2 and 11), and partially overlapping in the junction area 7".

Advantageously and as shown on FIGS. 7, 10, 12 and 16, the shifted or staggered arrangement of brackets or arm portions 7, 7' of the jaw or clamping members 3, as well as their relative positioning and guided displacement are such that, when moving the mobile body 6 to close the through hole 4, the brackets or arm portions 7, 7' engage each other so that an upper bracket or arm portion 7' of a given member 3 rests slidingly on a lower bracket or arm portion 7 of an other (immediately following) member 3, thus providing through mutual cooperation gripping portions 8 arranged on a tubular surface whose diameter depends on the closure ratio of the through hole 4.

As the overlaying length of the arm portions 7 and 7' at the junction area 7" is relatively small (in order to be able to achieve a through hole 4 of small diameter in the closed state of the device 1), a radial material thickening 8''' can be provided, in order to provide a sufficient mechanical strength, in particular as this area is subjected to high stress levels (in a clamped state of the device 1).

Figure 15C:
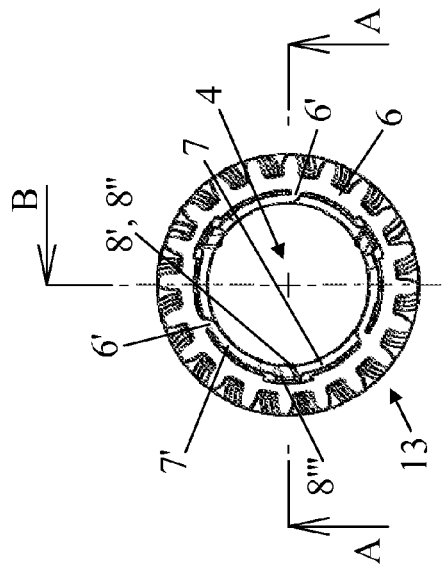
FIGS. 15A, 15B and 15C are views similar to FIGS. 12A, 12B and 12C respectively of a monolithic construction variant of the assembly (chuck unit)
Figure 15B:
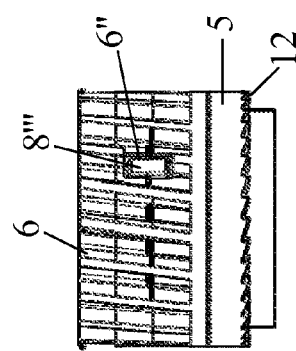

Said protruding material thickness 8''' can be received in a corresponding cutout or recesses 5", 6" in one of the bodies 5 or 6 when the chuck 13 is in its totally open state (FIGS. 9A and 15B).

Figure 1C:
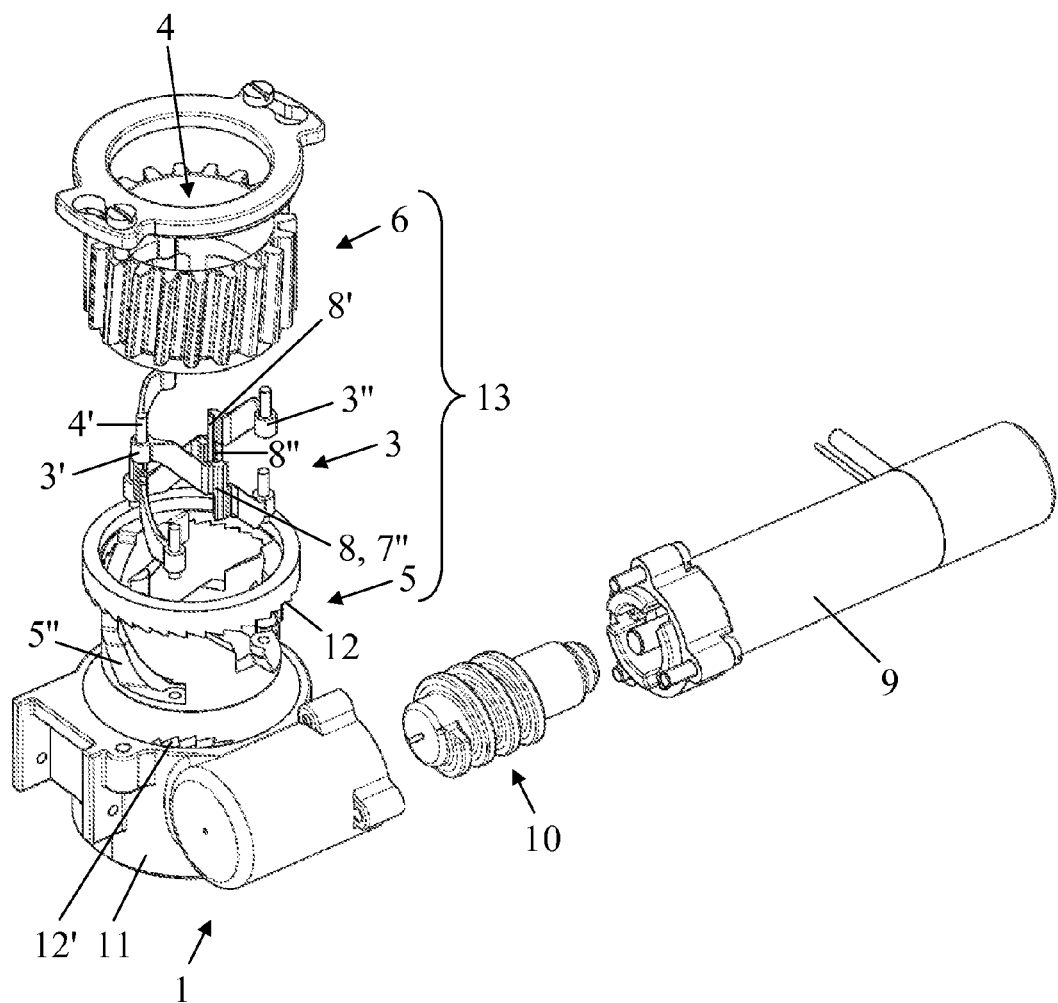
FIG. 1C is an exploded view of the device represented on FIGS. 1A and 1B.
Figure 3D:
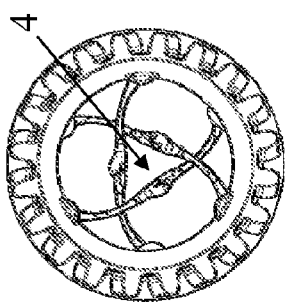
FIGS. 3A to 3D are top views of the chuck unit of a grasping device as shown on FIGS. 1A to 1C, in a completely opened state (FIG. 3A) and in various partially closed states (FIGS. 3B, 3C, 3D)
Figure 3C:
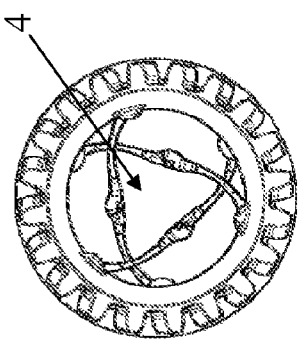
Figure 3B:
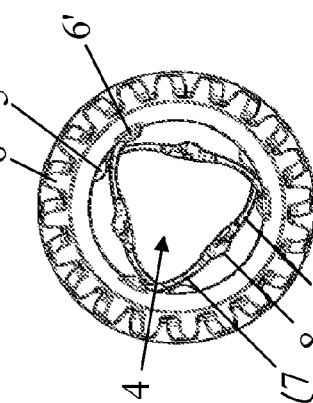
Figure 3A:
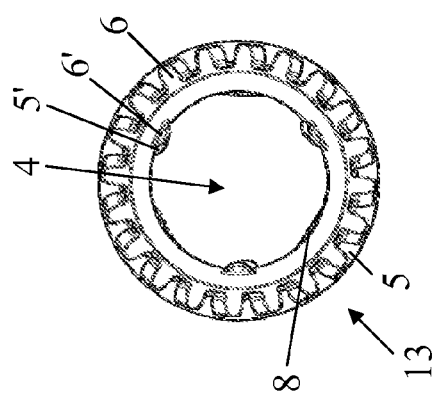
Figure 2:
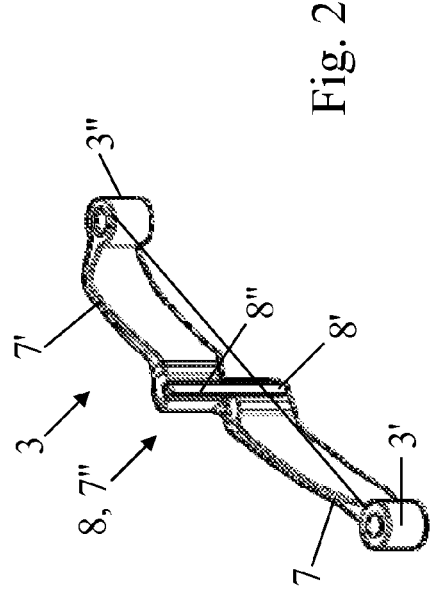
FIG. 2 is a perspective view of a jaw member of a device represented on FIGS. 1A, 1B and 1C.
Figure 6D:
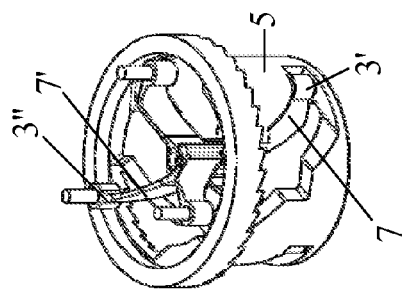
FIGS. 6A to 6D are perspective views respectively similar to the view of FIGS. 4A to 4D, the driving body having been removed.
Figure 6C:
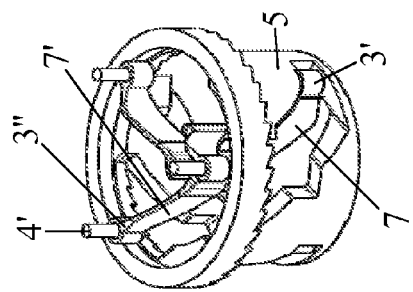
Figure 6B:
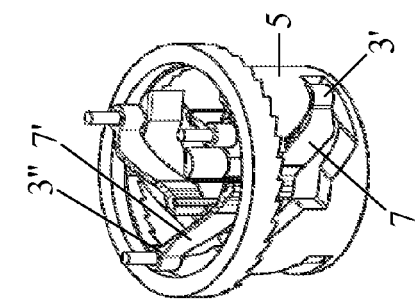
Figure 6A:
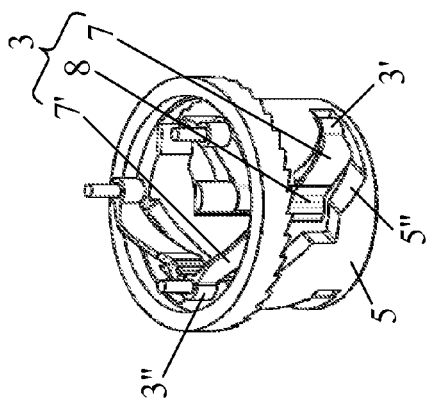
Figure 7D:
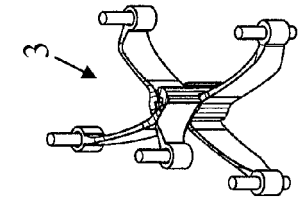
FIGS. 7A to 7D are perspective views respectively similar to the views of FIGS. 4A to 4D, the driving and the support bodies having been removed (only the jaw members are shown)
Figure 7C:
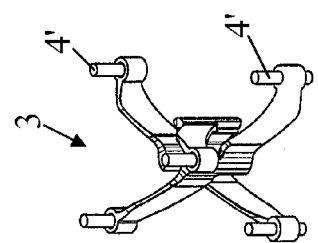
Figure 7B:
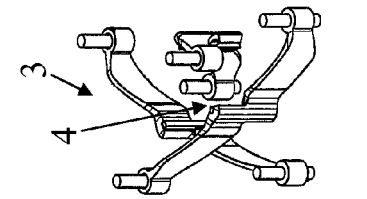
Figure 7A:
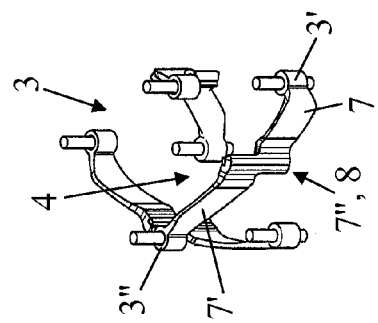

In a particular design, illustrated in FIGS. 1C, 2 and 7, each central gripping portion 8 can be comprised of two axially aligned clamping pads 8', 8" formed on the junction region 7" of the mutually connected abutting ends of the two brackets or arm portions 7, 7' and arranged in a staggered and rotationally shifted way, so as to constitute a substantially massive or solid body of twice the height of each jaw 8', 8" when said through hole 4 is substantially totally closed.

The gripping pads or coating can, for example, be made of Neoprene®.

Preferably, the jaw or clamping members 3 are made of a thermoplastic material (preferably compliant or resilient), the gripping portions 8 being preferably provided with overmolded high grip pads or coatings 8', 8". In a similar way, the bodies 5 and 6, as well as the casing 11 of the device 1 can be made in a hard thermoplastic material.

More precisely and as shown in FIGS. 2, 7, 9, 12, 13 and 14, the brackets or arm portions 7, 7' have a flexible constitution and preferably a substantially flat rectangular section (plate like shape), able to bend transversally or radially to the direction of the elongated body 2 to be grasped.

Figure 16B:
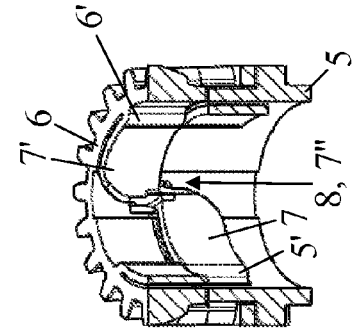
FIGS. 16A and 16B are sectional views along lines A-A and B-B of the item illustrated on FIG. 15C.
Figure 16A:
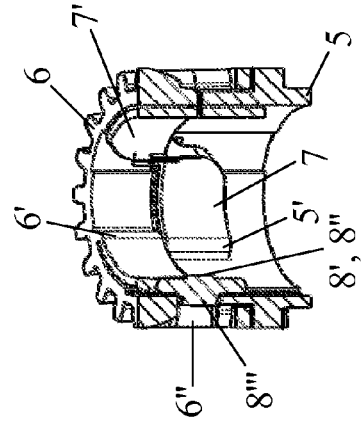
Figure 15A:
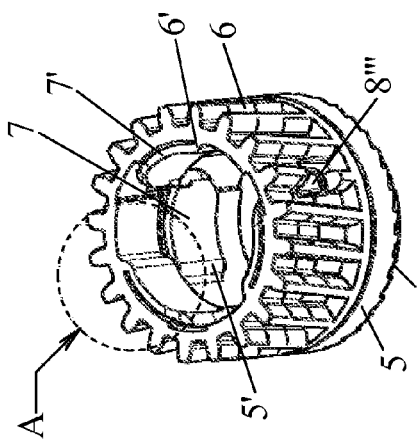
Figure 17:
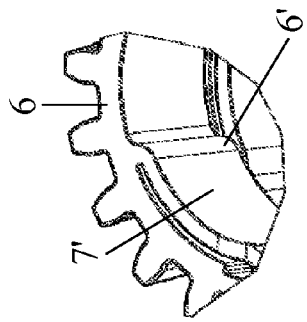
FIG. 17 is a detailed view at different scale of detail 1 of FIG. 15A.

According to an advantageous alternative practical embodiment of the invention, illustrated in FIGS. 15 to 17, the support body 5, the mobile body 6 and the jaw or clamping members 3 constitute a single-unit, monolithic or single block piece of thermoplastic material, or preferably of compatible thermoplastic materials of different qualities, properties and/or natures, the hinged or pivotal links 5', 6' being formed by film hinges or restricted material sections at the ends 3', 3" of the members 3. The rotation axis of the hinged links 5', 6' are in this case virtual axis.

Various ways and mechanisms for transmitting the driving movement to the body 6 in order to actuate the jaw members 3 can be considered.

As a first exemplary construction, shown in FIGS. 1C, 4, 5 and 8 to 10, the mobile annular driving body 6 consists of a gear or a similar externally teethed circular ring or tubular sleeve, arranged on top of the circular support body 5 and axially aligned with said body 5 preferably also in the shape of a ring or a tubular sleeve.

In accordance with a second alternative design, illustrated in FIGS. 19 to 21, the mobile annular driving body 6 has outside peripheral grooves 14, preferably arranged in a helicoïdal manner, said driving body 6 being arranged on top of the circular support body 5 and axially aligned with said body 5 preferably also in the shape of a ring or a tubular sleeve.

As shown in FIGS. 1A, 1B, 1C, 18, 19, 23 and 24, the driving body 6 is kinematically connected to an actuating means 9, for example an electric motor, the device 1 being thus motorized and able to be actuated in an automatic and controlled manner for example, either through a ball worm 10 and gear 6 link or through two cables 10' wound around the driving body 6 in opposite directions and arranged in corresponding grooves 14.

The device 1 may also comprise a casing 11 inside which the support body 5 and the driving body 6 forming the chuck unit 13 with the jaw members 3 are mounted, the body 6 being arranged with the ability of free rotation and said casing 11 possibly also supporting the actuating means 9, 10 of the driving body 6.

In order to allow a controlled rotation of the elongated body 2 when it is in a clamped state, but also ensure a reliable opening of the device 1 from a clamped state, the support body 5 and the casing 11 are in rotational engagement by means of asymmetric projections for example of two intermeshing teethed rings 12, 12', forming by cooperation a ratchet mechanism, the support body 5 being able to rotate with respect to the casing 11 when the torque applied to said support body 5, by the closing movement of the mobile body 6, is sufficient to disengage the two teethed rings and said support body 5 and said casing 11 being rotationally secured when said support body 5 is urged in the direction of the opening movement of the mobile body 6.

As shown in the operative sequences illustrated in FIGS. 3 to 7, 12 and 13 for a device 1 with three clamping members 3, when the device 1 passes from its completely open state to its completely closed state and vice-versa, the second end 3" of each of the three jaw members 3 linked to the driving body 6 moves along a circular arcuate path, of about 120 degrees, along the upper circular edge of the support body 5, when driven by said gear 6, the first end 3' of said member 3 experiencing simultaneously a pivotal movement about its hinged link with the support body 5, the concerned jaw member 3 thus realizing a lateral sweeping motion within the passage through the support and mobile bodies 5 and 6.

As the first end 3' follows the circular movement of driving body 6 and the second end 3" remains still (apart from a rotational movement around hinge 5'), the concerned member 3 and in particular central portion 8 is moved inwardly, away from the annular walls of the bodies 5 and 6 towards the central area of their inner cylindrical volume (FIGS. 3 and 13).

When the jaw members 3 are separately made pieces and in order to be able to provide a regular through hole 4 of maximum diameter, it is preferred that the support body 5 and/or the driving body 6 comprise(s) cutouts and/or recesses 5", 6" in its (their) cylindrical wall, able and adapted to receive and lodge at least partly, preferably completely, the jaw members 3 when the through hole 4 is open at its maximum.

As can be seen from the foregoing disclosure and exemplarily shown on the figures, the device 1 allows to pass from a completely open state to a completely closed state in a fraction of a turn only. With three members 3, a rotation of the body 6 of less than 120 degrees is sufficient.

The particular staggered configuration of the jaw members 3 allows a mutual resting of said members on each other, when the body 2 is clamped. This mutual interpenetration of the members 3 into each other, without interference with the opening and closing movement of said members 3, ensures an increased mechanical resistance to longitudinal constraint along the axis of the body 2.

The chuck unit 13 formed by the bodies 5 and 6 and the jaw members 3 can either be made in one single piece out of thermoplastic material(s), with compliant film hinges 5', 6' or be made by assembling the separately made elements 5, 6 and 3.

Various driving mechanisms can be used to transmit rotational torque to the driving body 6, such as a worm gear, antagonist cables or others operatively connected to an adapted actuator 9 (motor and possible associated reduction gear).

The body 6 can rotate relatively to the body 5 according to two opposed directions corresponding to the opening and the closure of the jaws 3. In the closing direction, the mutually cooperating arrangement projections 12, 12' ensure a limitation of the clamping force. After a threshold torque value has been reached, and as the rotation of body 6 in the closing direction continues, bodies 5 and 6 remain in a fixed position one towards the other and together they rotate with the clamped elongated body 2 with respect to the casing 11. This disposition allows to modify the angular orientation of body 2 along its axis, which is of interest in case of asymmetric tools such as surgical needles. In the opening direction, the asymmetric projections 12' of casing 11 engage the ones 12 of body 5 and prevent its rotation with body 6, thus allowing the jaw members 3 to untighten themselves.

When considering the jaw members 3 as at least radially deformable bodies, linked and articulated with both support and driving bodies 5 and 6 through pivot links 5', 6' with rotational axis parallel to the longitudinal axis of the device 1 (and thus of the grasped body 2), the closing of the device 1 causes a coordinated motion and deflection of the jaw members around body 2 (inwardly directed sweeping movement of the members 3 around their hinge 5' with support body 5).

Therefore a progressive and self adapting grip is achieved when the device 1 closes around body 2.

The present invention also concerns (not shown) a robotized installation for supporting and controlling the position and the transitional movement of an elongated body 2, such as a needle for example, wherein said robotized device comprises at least one or two spaced apart grasping device(s) 1, as described hereinbefore.

Such a robotized device or installation can, for example, be of the type disclosed in US 2008/0167663 (WO-A-2006/092496) and/or in US 2009/014907 (WO-A-2006/035143), the teachings of which are incorporated herein. Said robotized device can of course incorporate only one or two spaced apart and aligned grasping devices 1.

As it results from the foregoing description, the grasping device 1 according to the invention allows, with a simple structure, to provide a through hole with maximum width (substantially the same width than the support body 5 and the driving body 6), to keep safely the elongated body within a closed area and to regrasp and recenter easily the elongated body after releasing it.

Furthermore, the grasping device 1 according to the invention also allows to provide an important clamping force, in particular greater than that of the known rigid chuck unit.

The advantages, a practical working example, the behaviour and the superior performances (verified by tests) of the grasping device 1 according to the invention are at least partly mentioned in "Design, development and preliminary assessment of grasping devices for robotized medical applications", Piccin, O. et al., IDETC, ASME, Chicago, Aug. 12, 2012, whose content is incorporated herein.

The present invention is of course not limited to the preferred embodiments described and represented herein, changes can be made or equivalents used without departing from the scope of the invention.

The invention claimed is:

1. A device for selectively gripping or grasping a segment or part of a separate elongated body (2) extending through said device, the device (1) comprising:
    at least three, at least partially mobile jaw or clamping members (3), a through hole or receiving passage (4) defined between the jaw or clamping members (3) the through hole or receiving passage (4) being of variable diameter depending on mutual relative positioning of the jaw or clamping members (3),
    supporting and driving means (5, 6) to which said jaw or clamping members (3) are mounted and/or connected and which are adapted to provide a coordinated motion to said jaw or clamping members (3) around the elongated body (2) situated in the through hole or receiving passage (4), resulting in a closing or opening of said through hole or receiving passage (4),
    wherein each of the jaw or clamping members (3) is an elongated jaw or clamping member (3) having an elongated shape with opposed first and second opposed ends (3', 3"),
    wherein the supporting and driving means (5, 6) comprise a circular or annular support body (5) to which the first end (3') of each jaw or clamping member (3) is connected and a driving body (6) to which the second opposed end (3") of each jaw or clamping member (3) is connected, the driving body (6) being a mobile circular or annular driving body (6),
    wherein a rotational movement of the driving body (6) relative to the support body (5) results in a simultaneous and synchronous displacement of all the connected second ends (3") of the jaw or clamping members (3) and a corresponding variation of a size of the through hole or receiving passage (4),
    wherein each jaw or clamping member (3) has a gripping portion (8) for contacting to the elongated body (2) passing through the through hole or receiving passage (4), said gripping portion (8) being located centrally between the opposed first and second ends (3', 3") of said each jaw or clamping member (3), and
    wherein each jaw or clamping member (3) comprises a partly compliant or flexible elongated member comprising two arm portions (7, 7') arranged in an offset manner one towards the other, joined together at abutting ends and hinged respectively with the support body (5) and the driving body (6) at the opposed first and second ends (3', 3").

2. The device according to claim 1, wherein,
    the support body (5) is a fixed support body (5),
    the first end (3') of each jaw or clamping member (3) is hinged, around a hinged link (5'), with the support body (5), and
    each jaw or clamping member (3) is hinged at the first end (3') with the support body (5) and at the second end (3") with the driving body (6), a relative rotational movement of said driving body (6) with respect to the support body (5) inducing a rotational displacement of the first end (3'), around an axis of the hinged link (5'), with the support body (5) and a circular displacement of the second end (3") along a circular arc path supported by an inner circumference of the driving body (6).

3. The device according to claim 2, wherein the driving body (6) comprises a gear, an externally teethed circular ring, or a tubular sleeve, arranged on top of the support body (5) and axially aligned with said support body (5).

4. The device according to claim 3, wherein the second end (3") of each of the at least three jaw or clamping members (3) linked to the driving body (6) moves along a circular arcuate path, of about 120 degrees, along an upper circular edge of the support body (5) when driven by said gear, the first end (3') of said jaw or clamping member (3) experiencing simultaneously a pivotal movement about the hinged link with the support body (5), said jaw or clamping member (3) thus realizing a lateral sweeping motion within a passage through the support body (5) and the driving body (6).

5. The device according to claim 2, wherein the driving body (6) has outside peripheral grooves (14), said driving body (6) being arranged on top of the support body (5) and axially aligned with said support body (5).

6. The device according to claim 2, wherein the support body (5) and/or the driving body (6) comprise a cylindrical wall and cutouts and/or recesses (5", 6") in the cylindrical wall, able and adapted to receive and lodge, at least partly, the jaw or clamping members (3) when the through hole or receiving passage (4) is open at a maximum.

7. The device according to claim 1, wherein each arm portion (7, 7') is connected to the gripping portion (8) and provided at the opposed first and second ends (3', 3") with sites of hinged or pivotal links (5', 6') provided respectively on the support body (5) and on the driving body (6).

8. The device according to claim 7, wherein each elongated clamping member (3) has a staggered structure, the two arm portions (7, 7') being shifted one towards the other in an axial direction of the elongated body (2) when said elongated body is gripped by said jaw or clamping member clamping members (3) cooperating with each other.

9. The device according to claim 8, wherein the shifted arrangement of the two arm portions (7, 7') of the jaw or clamping members (3), as well as relative positioning and guided displacement of the two arm portions (7, 7') of the jaw or clamping members (3) are such that, when moving the driving body (6) to close the through hole or receiving passage (4), the two arm portions (7, 7') engage each other so that an upper one of the two arm portions (7') of a given one of the jaw or clamping members (3) rests slidingly on a lower one of the two arm portions (7) of another one of the jaw or clamping members (3), thus providing through mutual cooperation the gripping portions (8) arranged on a tubular surface whose diameter depends on a closure ratio of the through hole or receiving passage (4).

10. The device according to claim 7, wherein each gripping portion (8) is comprised of two axially aligned clamping pads (8', 8") formed on a junction region (7") of mutually connected abutting ends of the two arm portions (7, 7'), the two axially aligned clamping pads (8', 8") arranged in a staggered and rotationally shifted arrangement, so as to constitute a solid body of twice a height of each clamping pad (8', 8") when said through hole or receiving passage (4) is substantially totally closed.

11. The device according to claim 7, wherein the two arm portions (7, 7') have a flexible constitution and a flat rectangular section, able to bend transversally or radially to a direction of the elongated body (2) to be grasped.

12. The device according to claim 7, wherein the support body (5), the driving body (6) and the jaw or clamping members (3) constitute a single-unit, monolithic or single block piece of a thermoplastic material, the hinged or pivotal links (5', 6') being formed by film hinges or restricted material sections at the opposed first and second ends (3', 3") of the jaw or clamping members (3).

13. The device according to claim 12, wherein the driving body (6) is kinematically connected to an actuating means (9), the device (1) being thus motorized and able to be actuated in an automatic and controlled manner, either through a ball worm (10) and a gear link or through two cables (10') wound around the driving body (6) in opposite directions and arranged in grooves (14).

14. The device according to claim 13, further comprising a casing (11) inside which the support body (5) and the driving body (6) form a chuck unit (13) with the jaw or clamping members (3), the driving body (6) being arranged with an ability of free rotation and said casing (11) also supporting the actuating means (9) of the driving body (6).

15. The device according to claim 14, wherein the support body (5) and the casing (11) are in rotational engagement by asymmetric projections of two intermeshing teethed rings (12, 12'), formed by cooperation of a ratchet mechanism, the support body (5) being able to rotate with respect to the casing (11) when torque applied to said support body (5) by a closing movement of the driving body (6) is sufficient to disengage the two intermeshing teethed rings and said support body (5); and said casing (11) being rotationally secured when said support body (5) is urged in a direction of an opening movement of the driving body (6).

16. The device according to claim 1, wherein the arm portions (7, 7') are at least partly compliant in a radial direction and substantially rigid in an axial direction, when considered in relation to the elongated body (2), located and grasped within said device (1).

17. The device according to claim 1, wherein the jaw or clamping members (3) are made of a thermoplastic material, the gripping portions (8) being provided with high grip pads or coatings (8', 8").

18. A device for selectively gripping or grasping a segment or part of a separate elongated body (2) extending through said device, the device (1) comprising:
at least three, at least partially mobile jaw or clamping members (3), a through hole or receiving passage (4) defined between the jaw or clamping members (3) the through hole or receiving passage (4) being of variable diameter depending on mutual relative positioning of the jaw or clamping members (3); and
supporting and driving means (5, 6) to which said jaw or clamping members (3) are mounted and/or connected and which are adapted to provide a coordinated motion to said jaw or clamping members (3) around the elongated body (2) situated in the through hole or receiving passage (4), resulting in a closing or opening of said through hole or receiving passage (4) device (1),
wherein each of the jaw or clamping members (3) is an elongated jaw or clamping member (3) having an elongated shape with opposed first and second opposed ends (3', 3"),
wherein the supporting and driving means (5, 6) comprise a circular or annular support body (5) to which the first end (3') of each jaw or clamping member (3) is connected and a driving body (6) to which the second opposed end (3") of each jaw or clamping member (3) is connected, the driving body (6) being a mobile circular or annular driving body (6), wherein a rotational movement of the driving body (6) relative to the support body (5) results in a simultaneous and synchronous displacement of all the connected second ends (3") of the jaw or clamping members (3) and a corresponding variation of a size of the through hole or receiving passage (4), wherein each jaw or clamping member (3) has a gripping portion (8) for contacting to the elongated body (2) passing through the through hole or receiving passage (4), said gripping portion (8) being located centrally between the opposed first and second ends (3', 3") of said each jaw or clamping member (3), wherein the elongated jaw or clamping members (3) are mutually arranged and connected by the opposed first and second ends (3' and 3") respectively to the support body (5) that the driving body (6) respectively in such a way that said elongated jaw or clamping members (3) always extend continually around the through hole or receiving passage (4), thus defining a peripherally closed hole or passage (4) whatever a state of opening or closure of the device (1), and wherein each jaw or clamping member (3) comprises a partly compliant or flexible elongated member comprising two arm portions (7, 7') arranged in an offset manner one towards the other, joined together at abutting ends and hinged respectively with the support body (5) and the and driving body (6) at the opposed first and second ends (3', 3"), at least a part.

19. A surgical device for selectively gripping or grasping a segment or part of a separate elongated body (2) extending through said device, the surgical device (1) comprising:

at least three, at least partially mobile jaw or clamping members (3), a through hole or receiving passage (4) defined between the jaw or clamping members (3) the through hole or receiving passage (4) being of variable diameter depending on mutual relative positioning of the jaw or clamping members (3); and supporting and driving means (5, 6) to which said jaw or clamping members (3) are mounted and/or connected and which are adapted to provide a coordinated motion to said jaw or clamping members (3) around the elongated body (2) situated in the through hole or receiving passage (4), resulting in a closing or opening of said through hole or receiving passage (4) device (1), wherein each of the jaw or clamping members (3) is an elongated jaw or clamping member (3) having an elongated shape with opposed first and second opposed ends (3', 3"), wherein the supporting and driving means (5, 6) comprise a circular or annular support body (5) to which the first end (3') of each jaw or clamping member (3) is connected and a driving body (6) to which the second opposed end (3") of each jaw or clamping member (3) is connected, the driving body (6) being a mobile circular or annular driving body (6), the support body (5) being a fixed support body (5), wherein a rotational movement of the driving body (6) relative to the support body (5) results in a simultaneous and synchronous displacement of all the connected second ends (3") of the jaw or clamping members (3) and a corresponding variation of a size of the through hole or receiving passage (4), wherein each jaw or clamping member (3) has a gripping portion (8) for contacting to the elongated body (2) passing through the through hole or receiving passage (4), said gripping portion (8) being located centrally between the opposed first and second ends (3', 3") of said each jaw or clamping member (3), wherein the elongated jaw or clamping members (3) are mutually arranged and connected by the opposed first and second ends (3' and 3") respectively to the support body (5) that the driving body (6) respectively in such a way that said elongated jaw or clamping members (3) always extend continually around the through hole or receiving passage (4), thus defining a peripherally closed hole or passage (4) whatever a state of opening or closure of the surgical device (1), and wherein each jaw or clamping member (3) comprises a partly compliant or flexible elongated member comprising two arm portions (7, 7') arranged in an offset manner one towards the other, joined together at abutting ends and hinged respectively with the support body (5) and the and driving body (6) at the opposed first and second ends (3', 3"), at least a part.

* * * * *